United States Patent [19]

Astheimer et al.

[11] 4,294,666
[45] Oct. 13, 1981

[54] PROCESS FOR THE MANUFACTURE OF 4,4'-DIPHENYL-METHANE DIISOCYANATE AND A MIXTURE OF DIPHENYL-METHANE DIISOCYANATE ISOMERS CONTAINING A SMALL AMOUNT OF URETDIONES AND HYDROLYZABLE CHLORINE

[75] Inventors: Hans J. Astheimer, Neuhofen; Horst Brandtstaedter, Ludwigshafen; Rainer Ohlinger, Heidelberg, all of Fed. Rep. of Germany; Willy Van Pee, Ekeren; Jaak Van Steen, Wuustwezel, both of Belgium; Friedrich Sauer, Obersuelzen, Fed. Rep. of Germany; Rudolf Schmidt, Frankenthal, Fed. Rep. of Germany; Siegfried Krueger, Speyer, Fed. Rep. of Germany

[73] Assignee: BASF Aktiengesellschaft, Ludwigshafen, Fed. Rep. of Germany

[21] Appl. No.: 178,673

[22] Filed: Aug. 15, 1980

[30] Foreign Application Priority Data

Aug. 18, 1979 [DE] Fed. Rep. of Germany ....... 2933601

[51] Int. Cl.$^3$ .................... B01D 3/10; C07C 119/048

[52] U.S. Cl. ........................................ 203/72; 203/74; 203/75; 203/81; 203/82; 203/87; 260/453 SP; 260/453 AM

[58] Field of Search ................ 260/453 SP, 453 AM; 203/72, 81, 87

[56] References Cited

U.S. PATENT DOCUMENTS

| | | | |
|---|---|---|---|
| 3,658,656 | 4/1972 | Adica et al. | 203/49 |
| 3,857,871 | 12/1974 | Hatfield et al. | 260/453 SP |
| 4,118,410 | 10/1978 | Friedel et al. | 260/453 AM |
| 4,189,354 | 2/1980 | Ellendt et al. | 203/81 |

Primary Examiner—Dolph H. Torrence
Attorney, Agent, or Firm—H. Lawrence Jones

[57] ABSTRACT

A process for the manufacture of 4,4'-diphenylmethane diisocyanate and a mixture of diphenylmethane diisocyanate isomers containing a controllable amount of uretdione and hydrolizable chlorine which comprises feeding crude MDI to an evaporator, condensing a head fraction in two stages in the presence of an inert gas, feeding the first stage condensate to a distillation column, producing a mixture of diphenylmethane diisocyanate isomers as an overhead, producing 4,4'-diphenylmethane diisocyanate as a side draw, and condensing each of the overhead and side draw in two stages in the presence of an inert gas.

6 Claims, 3 Drawing Figures

PROCESS FOR THE MANUFACTURE OF 4,4'-DIPHENYL-METHANE DIISOCYANATE AND A MIXTURE OF DIPHENYL-METHANE DIISOCYANATE ISOMERS CONTAINING A SMALL AMOUNT OF URETDIONES AND HYDROLYZABLE CHLORINE

BACKGROUND OF THE INVENTION

1. Field of the Invention

This invention relates to a process for the manufacture of mixtures of diphenylmethane diisocyanate isomers, particularly of mixtures consisting of 2,4'- and 4,4'-diphenylmethane diisocyanates, as well as pure MDI, 4,4'-diphenylmethane diisocyanate, containing a small amount of uretdiones and hydrolyzable chlorine by distillation of crude MDI. The crude MDI is a mixture of diphenylmethane diisocyanates and polyphenylene polymethylene polyisocyanates, in which the distillable diphenylmethane diisocyanate isomer mixtures and/or the 4,4'-diphenylmethane diisocyanate are/is condensed in two stages, possibly in the presence of an inert gas.

2. Description of the Prior Art

In addition to crude MDI, 2,4'-diphenylmethane diisocyanate, and particularly pure MDI, 4,4'-diphenylmethane diisocyanate, are important raw materials for the manufacture of polyurethane plastics.

A number of methods are known which describe the simultaneous manufacture of pure MDI and polyphenylene polymethylene polyisocyanates. German application No. 15 93 638, German application No. 16 43 093, German application No. 19 23 214, and German Published application No. 24 04 170 relate to distillation processes for the separation of crude MDI.

According to German Published application No. 21 05 193 and German Published application No. 24 25 658, the diphenylmethane diisocyanate isomers are initially distilled from the crude MDI and are then separated into pure MDI and a mixture of 2,4'- and 4,4'-diphenylmethane diisocyanate by fractional crystallization.

A drawback of the described processes is that the resultant isocyanates contain varying quantities of uretdiones and chlorine compounds as byproducts.

Uretdiones are produced in a temperature dependent equilibrium by containing dimerization of 4,4'-diphenylmethane diisocyanate at the NCO groups. Uretdiones form insoluble crystals in pure MDI plugging lines, equipment and machinery during processing.

Organic chlorine compounds are generally detrimental if they are converted into compounds with easily hydrolyzable chlorine at elevated temperatures. Hydrolyzable chlorine compounds, particularly when they occur in varying concentrations, interfere with the reaction of isocyanates with polyols resulting in polyurethanes since the rate of reaction is influenced by the chlorine compounds. In addition to this, they cause a more rapid yellow discoloration of the initially water clear and colorless isocyanates. It is difficult to analytically differentiate among the individual chlorine compounds. The following are mentioned as possible compounds: phosgene, N,N-dimethylaniline hydrochloride, N-chloroformylaniline, N-methyl-N-chloroformylaniline, as well as compounds having the formulas:

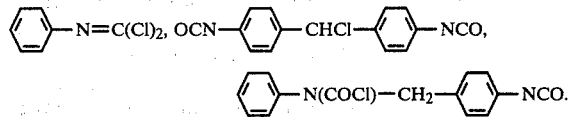

In order to reduce the concentration of hydrolyzable chlorine, it has been suggested that the organic isocyanates, possibly in the presence of metal compounds, are heated to increased temperatures (U.S. Pat. Nos. 3,155,699, 3,264,336 and German application No. 12 70 036) and that they are subsequently distilled or that the chlorine compounds are separated by a commercially expensive fractional crystallization (German Published application No. 19 38 384).

In order to separate crude MDI and to manufacture diphenylmethane diisocyanate isomers having an adjusted chlorine content, the materials are subjected to a 4 or 5 fold fractional distillation in accordance with German application No. 26 31 168. According to data in this publication (FIG. 3), the diphenylmethane diisocyanate isomers are removed from the crude MDI by distillation in the first column. The diphenylmethane diisocyanate isomers are then separated in a second column from small quantities of distilled over 3-nuclei oligomers and hard to volatilize compounds containing hydrolyzable chlorine. In a third column, the lower-boiling chlorine compounds, which are distilled off as head fractions, are separated from the diphenylmethane diisocyanate isomers. The diphenylmethane diisocyanate isomers consisting of 2,4' and 4,4'-diphenylmethane diisocyanates are subjected to another distillation for the purpose of separating the isomers whereby the lower-boiling 2,4'-diphenylmethane diisocyanate is distilled overhead. In a last distillation stage, the remaining 4,4'-diphenylmethane diisocyanate must then be separated from the polymer components produced during the distillation. A drawback of this method is that the thermally sensitive isocyanates polymerize during the multiple distillation, thus forming a relatively large polymeric residue.

SUMMARY OF THE INVENTION

The object of this invention is to produce carefully regulated products which are a mixture of diphenylmethane diisocyanate isomers, particularly a mixture of 2,4'- and 4,4'-diphenylmethane diisocyanates, and 4,4'-diphenylmethane diisocyanate, containing a small amount of uretdiones and hydrolyzable chlorine, requiring low equipment expenditures. Surprisingly, the object of this invention is met by a process which comprises feeding crude MDI to an evaporator, condensing a head fraction in two stages, optionally in the presence of an inert gas in a condensation stage I, and optionally distilling a fraction I condensate of condensation stage I in a subsequent distillation column which further comprises condensing pure MDI in a side fraction, optionally in two stages, optionally in the presence of an inert gas and condensing an overhead fraction, optionally in two stages, optionally in the presence of an inert gas.

DESCRIPTION OF THE PREFERRED EMBODIMENTS

The object of this invention is met by a process for the manufacture of a mixture of diphenylmethane diisocyanate isomers and particularly 4,4'-diphenylmethane diisocyanate containing a small amount of uretdiones and hydrolyzable chlorine by distilling a mixture of crude MDI, diphenylmethane diisocyanate isomers and polyphenylene polymethylene polyisocyanates, which comprises:

A. feeding crude MDI into an evaporator at temperatures of 175° C. to 200° C. under reduced pressure, B. discharging a non-distilled bottom fraction of from 97 weight percent to 50 weight percent based on the feed amount of crude MDI, C. evaporating a head fraction of from 3 weight percent to 50 weight percent based on the feed amount of crude MDI, D. condensing from the head fraction, a fraction I of from 90 weight percent to 99 weight percent based on the feed amount of the head fraction, in a condensation stage I, at a temperature of from 130° C. to 170° C., the fraction I containing at least 96 weight percent, based on the weight of fraction I, of diphenylmethane diisocyanate isomers, less than one weight percent, based on the weight of fraction I, of uretdiones and less than 50 ppm, based on the weight of fraction I, of hydrolyzable chlorine compounds, and E. condensing the remaining 10 weight percent to one weight percent, based on the feed amount of head fraction, in a condensation stage II at a temperature of from 45° C. to 60° C.

In a preferred embodiment of this invention, an inert gas, preferably nitrogen, is countercurrently fed through condensation stage I.

In a preferred embodiment of this invention, fraction I is separated in a subsequent distillation column which further comprises condensing the side fraction, optionally in two stages and in the presence of an inert gas, condensing the overhead fraction, optionally in two stages and in the presence of an inert gas, and discharging a sump fraction.

In another preferred embodiment, the side fraction of the distillation column is condensed in the first stage at a temperature of from 130° C. to 170° C. and in the second stage at a temperature of from 45° C. to 60° C.

In another preferred embodiment, the remaining head fraction from the evaporator and the second condensation stage feed of the overhead fraction and side fraction of the distillation column are combined and condensed in a condensor.

In another preferred embodiment, an inert gas, preferably nitrogen, is fed through the evaporator.

The most important versions of the process of this invention are explained in greater detail in the illustrations.

Figure 1:
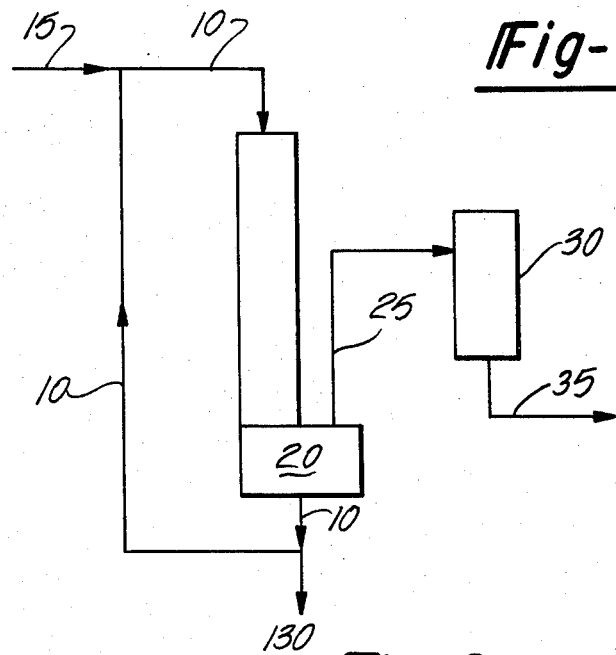

FIG. 1 corresponds with a method according to the current state of the art. In this illustration, (20) represents a distillation stage in which the mixture of diphenylmethane diisocyanate isomers is separated from the crude MDI with the aid of a thin film evaporator. Fresh crude MDI is added to a non-distilled bottom fraction (10) via feed line (15). An undistilled bottom fraction may be removed via discharge line (130). The vapors (25) distilled off the thin film evaporator, consisting of 2,2'-, 2,4'- and 4,4'-diphenylmethane diisocyanate isomers, are liquified in one stage in the condenser (30) and are removed via discharge line (35).

Figure 2:
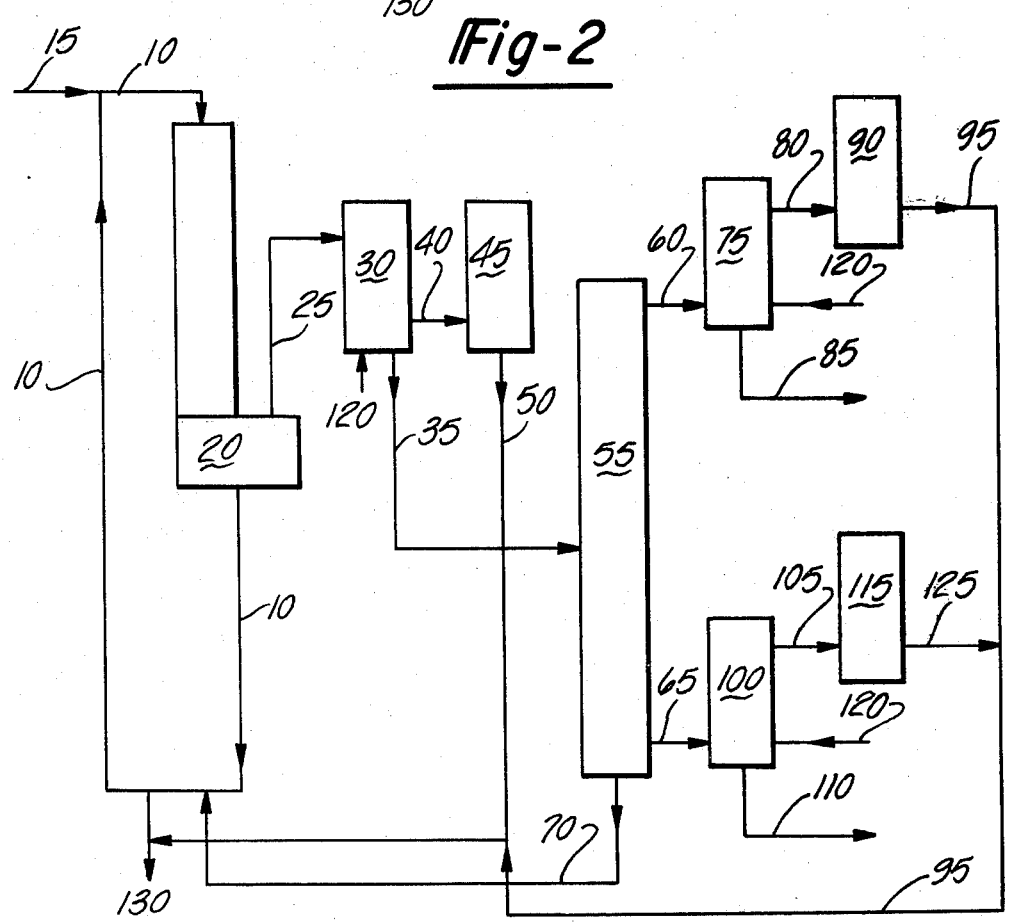

FIG. 2 shows a preferred embodiment of the process of this invention. In the thin film evaporator (20), the crude MDI is separated into a non-distilled bottom fraction (10) and a head fraction (25) which primarily consists of diphenylmethane diisocyanate isomers, 3- nuclei oligomers such as 1-(4-isocyanato-phenylmethyl)-3-(2-isocyanato-phenylmethyl)-4-isocyanatobenzene and hydrolyzable chlorine compounds. The non-distilled bottom fraction (10) from which discharge can be removed via discharge line (130) is recycled and fresh crude MDI can be added via feed line (15). The head fraction (25) is condensed in two stages in condensers (30) and (45) in which 90 weight percent to 99 weight percent, preferably 94 weight percent to 96 weight percent, relative to the total weight of the head fraction, is liquified to fraction I (35) in the condensation stage I in condenser (30), preferably in the presence of an inert gas (120) and the remaining 10 weight percent to 1 weight percent, preferably 6 weight percent to 4 weight percent, relative to the total weight of the head fraction is fed to condenser (45) via feed line (40) where they are condensed in condensation stage II and via discharge line (50) is added to discharge line (130).

Fraction I, which contains at least 96 weight percent, relative to the total weight of diphenylmethane diisocyanate isomers, preferably 2,4'- and 4,4'-diphenylmethane diisocyanate, in a weight ratio of 10:90 to 3:97 and which shows less than 1 weight percent, preferably 0.3 weight percent to 0.7 weight percent, of uretdione and less than 50 ppm, preferably between 1 ppm and 20 ppm, of hydrolyzable chlorine is separated, preferably in the subsequent distillation column (55), into an overhead fraction (60), a side fraction (65), and a sump fraction (70) which is incorporated in the non-distilled bottom fraction (10). The overhead fraction (60) which primarily consists of a mixture of 2,4'- and 4,4'-diphenylmethane diisocyanate in a weight ratio of 30:70 to 50:50, preferably 38:62 to 45:55, and the side fraction (65) which consists of 4,4'-diphenylmethane diisocyanate having a purity of approximately 99 percent are preferably condensed also in two stages in condensers (75) and (90), and (100) and (115), respectively. In the two first stages, (75) and (100), preferably in the presence of an inert gas (120), 90 weight percent to 99 weight percent, preferably 94 weight percent to 96 weight percent, relative to the total weight of the overhead or side fraction, are liquified and are discharged via discharge lines (85) and (110), respectively. The remaining 10 weight percent to 1 weight percent, preferably 6 weight percent to 4 weight percent, of the fed overhead or side fraction, is fed into the condensers (90) and (115) via feed lines (80) and (105), subjected to a second condensation stage, discharged via discharge lines (95) and (125), combined, and added to discharge line (130).

Figure 3:
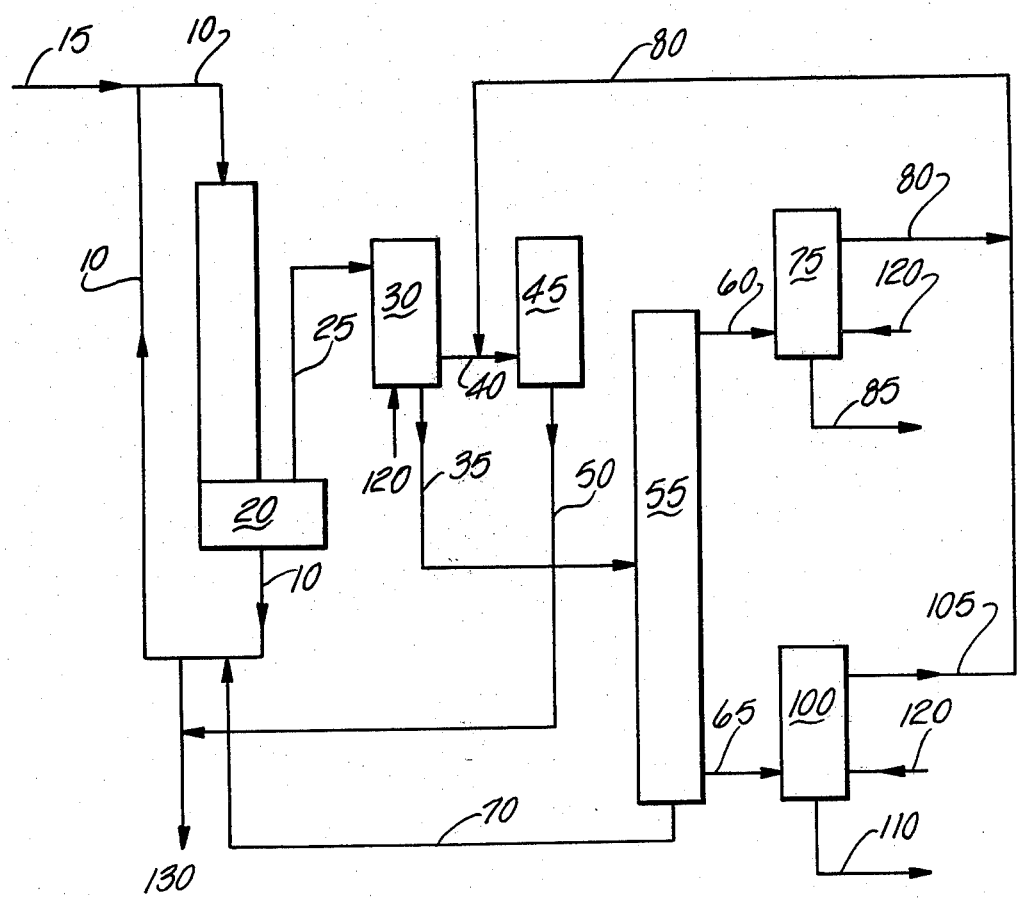

FIG. 3 shows another preferred embodiment of the process according to this invention. The vapors of condensers (30), (75) and (100), which were not condensed in condensation stage I of the head fraction, and in the first condensation stages of the overhead and side fractions, are combined via discharge lines (40), (80) and (105) and are jointly fed into condenser (45) where they are liquified in condensation stage II and via discharge line (50) are incorporated in the discharge of discharge line (130).

The required reaction conditions in the individual reaction stages to implement the process of this invention are set forth below.

Regular crude MDI, which is obtained by the condensation of aniline and formaldehyde in the presence of acid catalysts and the subsequent conversion of the resulting mixture of diphenylmethane diamines and polyphenylene polymethylene polyamines with phosgene, is suitable for the manufacture of mixtures of diphenylmethane diisocyanate isomers, particularly of mixtures consisting of 2,4'- and 4,4'-diphenylmethane diisocyanate as well as pure 4,4'-diphenylmethane diisocyanate according to the process of this invention. Preferably used are crude MDI mixtures containing 80 weight percent to 40 weight percent, preferably 80 weight percent to 50 weight percent, and more preferably 75 weight percent to 60 weight percent, based on the weight of crude MDI, of diphenylmethane diisocyanate isomers. The 4,4'-diphenylmethane diisocyanate content amounts to 90 weight percent to 98 weight percent, preferably 94 weight percent to 96 weight percent, relative to the weight of diphenylmethane diisocyanate isomers. The manufacture of such crude MDI mixtures is described, for instance, in the following patents: German Published application No. 15 93 638, British Pat. No. 648,787 and Canadian Pat. No. 700,026.

As already mentioned, the crude MDI, having a content of hydrolyzable chlorine of approximately 400 ppm to 1000 ppm, preferably of 450 ppm to 550 ppm, is separated in an evaporator such as a thin-film evaporator or a falling-film evaporator, preferably in a falling-film evaporator, at temperatures of 175° C. to 210° C., preferably 180° C. to 196° C., under reduced pressure, for instance at 2 millibars to 10 millibars, preferably 2 millibars to 6 millibars. Of the introduced crude MDI, 97 weight percent to 50 weight percent, preferably 85 weight percent to 60 weight percent, are discharged as non-distilled bottom fraction and 3 weight percent to 50 weight percent, preferably 15 weight percent to 40 weight percent, are distilled off as head fraction. If required, the distillation may be carried out in the presence of gases which are inert with respect to isocyanates under the reaction conditions. Examples of these gases include carbon dioxide and argon and, particularly, nitrogen. The amount of inert gas fed to the thin film evaporator per kilogram per hour of feed crude MDI is 0 NL/h to 5 NL/h, preferably 1 NL/h to 2 NL/h.

The head fraction is now condensed in two stages whereby 90 weight percent to 99 weight percent, preferably 94 weight percent to 96 weight percent, relative to the total weight of the feed head fraction is liquified in condensation stage I at temperatures from 130° C. to 170° C., preferably 155° C. to 165° C., and pressures of 2 millibars to 10 millibars, preferably 2 millibars to 6 millibars. The condensation is preferably carried out in the presence of one of the above-mentioned inert gases which are advantageously directed through the condenser (30) as a counter current. This not only accelerates the cooling of the condensates and reduces the formation of uretdione in fraction I but also aids in discharging the easier volatilized materials, particularly chlorine-containing compounds. Used on an average are 0 to 5 NL/h, preferably 1 to 2 NL/h inert gas per kilogram/h of feed head fraction.

To further reduce the uretdione content, the condensates of condensation stage I may also be mixed with cooled fraction I in a subsequent device, for instance a mixer, and the product can thus be cooled quickly to temperatures below 60° C., preferably 50° C. to 40° C.

The remaining 10 weight percent to 1 weight percent, preferably 6 weight percent to 4 weight percent, relative to the total weight of the feed head fraction is liquified in condensation stage II in condenser (45) at temperatures of 45° C. to 60° C., preferably of 50° C. to 55° C., and pressures of 2 millibars to 10 millibars, preferably 3 millibars to 5 millibars. The condensate of condensation stage II, which is normally incorporated in the discharge (130) of the non-distilled bottom fraction, contains more than 95 weight percent of diphenylmethane diisocyanate isomers including approximately 80 weight percent to 95 weight percent 4,4'-diphenylmethane diisocyanate and approximately 20 weight percent to 5 weight percent 2,4'-diphenylmethane diisocyanate; 0.2 weight percent to 0.7 weight percent uretdiones, preferably 0.3 weight percent to 0.5 weight percent; and also the predominant part of the hydrolyzable chlorine.

Fraction I containing, as already described, at least 96 weight percent preferably 2,4'- and 4,4'-diphenylmethane diisocyanate, with preferably less than 0.7 weight percent of uretdiones and less than 20 ppm hydrolyzable chlorine, is preferably fractionated in a subsequent distillation column. Advantageously used for this purpose is a multi-stage distillation column which has only a slight pressure loss and which has a theoretical number of plates of approximately 7 to 10 in the rectifying section, and a theoretical number of plates of 10 to 15 in the stripping section. The temperature in the distillation column at the column head is 170° C. to 210° C., preferably 190° C. to 200° C., and in the column sump, 190° C. to 230° C., preferably 200° C. to 210° C. The distillation is carried out under reduced pressure of 1 millibar to 25 millibars, preferably of 3 millibars to 12 millibars, possibly in the presence of inert gases. The reflux ratio (the volume ratio of reflux to distillate removal) is from 5 to 20, preferably from 10 to 15.

Fraction I is fed into the distillation column between the rectifying and stripping section. At the column head, overhead fraction (60), a mixture of 2,4'- and 4,4'-diphenylmethane diisocyanate is produced; at the lower end of the stripping section, side fraction (65), nearly pure 4,4'-diphenylmethane diisocyanate is produced; and in the sump, sump fraction (70), a mixture of 4,4'-diphenylmethane diisocyanate, 3-nuclei oligomers, the cleavage and polymerization products are discharged. The overhead, side and sump fractions also contain hydrolyzable chlorine compounds. The sump fraction contains the higher-boiling, hard-to-separate chlorine compounds and the overhead and side fractions contain the lower-boiling and separable chlorine compounds. The sump fraction is the bottom or pot fraction of the distillation column. The non-distilled bottom fraction is the residue removed from the bottom of the evaporator. The undistilled bottom fraction is the fraction which is removed from the undistilled bottom fraction discharge line (130).

For the manufacture of mixtures of 2,4'- and 4,4'-diphenylmethane diisocyanates or 4,4'-diphenylmethane diisocyanate containing a small amount of uretdiones and hydrolizable chlorine, the overhead fractions are condensed in two stages and the side fraction is condensed in two stages in the absence or preferably, in the the presence, of inert gases of the above-mentioned type. If the overhead and side fractions are condensed in two stages, 90 weight percent to 99 weight percent, preferably 94 weight percent to 96 weight percent, respectively, of the feed vapors is liquified in the first condensation stage in condensers (75) or (100) at temperatures of 130° C. to 180° C., preferably of 160° C. to 170° C., and pressures of 2 millibars to 10 millibars, preferably 2 millibars to 6 millibars. The feed amount of inert gas is approximately 2 NL/h to 7 NL/h, preferably 4 NL/h to 5 NL/h, per kilogram/hour of feed overhead or side fraction. The remaining 10 weight percent to 1 weight percent, preferably 6 weight percent to 4 weight percent, of the overhead or side fraction are condensed in the second condensation stage in condensers (90) or (115) at temperatures of 45° C. to 60° C., preferably of 50° C. to 55° C., and pressures of 2 millibars to 10 millibars, preferably of 3 millibars to 5 millibars.

If the overhead fraction is liquified in a single stage, the condensation preferably takes place in the presence of inert gases. The condensation temperatures are then 45° C. to 60° C., preferably 50° C. to 55° C., and the pressures are 2 millibar to 6 millibars, preferably 3 millibar to 5 millibars.

The condensates of the first and second condensation stages of the overhead and side fractions have the following average product composition.

The overhead fraction, first condensation stage, condensate line (85) is a mixture of 2,4'- and 4,4'-diphenylmethane diisocyanates containing at least 99 weight percent of diphenylmethane diisocyanate isomers and has a weight ratio of 2,4'-:4,4'- isomers of 10:90 to 50:50, preferably of 25:75 to 35:65. The uretdione content of the mixture is less than 0.5 weight percent, preferably between 0.1 weight percent to 0.3 weight percent, and the hydrolyzable chlorine content is less than 50 ppm, preferably between 20 ppm and 30 ppm.

The overhead fraction, second condensation stage, condensate line (95) is a mixture of 2,4'- and 4,4'-diphenylmethane diisocyanates having a diphenylmethane diisocyanate isomer content of at least 99 weight percent and a weight ratio of 2,4'-:4,4'- isomers of 10:90 to 50:50. The uretdione content of the mixture is less than 0.5 weight percent and the hydrolyzable chlorine content is less than 500 ppm, preferably 200 ppm to 300 ppm.

The side fraction, first condensation stage, product line (110) is a 4,4'-diphenylmethane diisocyanate having a degree of purity of at least 99 weight percent, a uretdione content of less than 0.25 weight percent, and a hydrolyzable chlorine content of less than 10 ppm, preferably between 1 ppm to 5 ppm.

The side fraction, second condensation stage, condensate line (125) is a 4,4'-diphenylmethane diisocyanate having a degree of purity of at least 99 weight percent, a uretdione content of less than 0.5 weight percent, preferably of 0.3 weight percent to 0.4 weight percent, and a hydrolyzable chlorine content of less than 500 ppm, preferably of 250 ppm to 300 ppm.

The mixtures of diphenylmethane diisocyanate isomers, produced in accordance with this invention, particularly those of 2,4'- and 4,4'-diphenylmethane diisocyanate, are very well suited for the manufacture of polyurethane adhesives and coatings. Pure 4,4'-diphenylmethane diisocyanate is used on a preferred basis for the manufacture of polyurethane elastomers, polyurethane threads, and bristles. Due to the low hydrolyzable chlorine content, the polyurethanes are relatively resistant to yellowing upon exposure to air and light.

EXAMPLES 1 AND 2

A mixture of diphenylmethane diisocyanates and polyphenylene polymethylene polyisocyanates is separated in a falling film evaporator, in the presence of nitrogen as inert gas (Example 2), into a non-distilled bottom fraction and a head fraction with the vapors of the head fraction being condensed in two stages. 94 Percent of the vapors are liquified in condensation stage I.

In the comparison example, crude MDI is fed into the evaporator and the product condensed in one stage.

In Example 1, crude MDI is fed to the evaporator and the product condensed in two stages.

In Example 2, crude MDI is fed to the evaporator, nitrogen is fed to the evaporator, and the product condensed in two stages.

The data of Table 2 shows that, when compared with the comparison example, the process of the invention has reduced content of hydrolyzable chlorine.

The reaction conditions are summarized in Table 1. The composition of the product streams is summarized in Table 2.

TABLE 1

Examples 1, 2 and Comparison Example (single-stage condensation) Reaction Conditions

| Example | | 1 | 2 | Comparison Example |
|---|---|---|---|---|
| Feed quantity | [kg/h] | 47 | 62 | 49.9 |
| Discharged amount of non-distilled bottom fraction | [kg/h] | 31 | 43 | 35.2 |
| Head fraction (total distillate quantity) | [kg/h] | 16 | 17 | 14.6 |
| Condensation stage I Fraction I (35) | [kg/h] | 15 | 16 | — |
| Condensation stage II Condensate (50) | [kg/h] | 1 | 1 | — |
| Circulating quantity | [kg/h] | 1000 | 1000 | 1000 |
| Nitrogen quantity introduced at the head of the falling film evaporator | [NL/h] | — | 180 | — |
| Falling film evaporator: | | | | |
| Feed temperature | [°C.] | 180 | 180 | 180 |
| Sump Temperature | [°C.] | 186 | 195 | 196 |
| Pressure | [mbar] | 3 | 2 | 3 |
| Condensation temperature: | | | | |
| Condensation stage I | [°C.] | 140 | 138 | 45 |
| Condensation stage II | [°C.] | 45 | 45 | — |

TABLE 2

Composition of Product Streams

| | Diphenylmethane-Diisocyanate Isomers | | | Polyphenylene-Polymethylene-Polyisocyanate Oligomers With | | | Hydrolyzable | |
|---|---|---|---|---|---|---|---|---|
| | Total % | 2,4'- % | 4,4'- % | 3-nuclei % | 4-nuclei % | 5-nuclei % | Chlorine ppm | Uretdiones % |
| Example 1: | | | | | | | | |
| Feed | 53.1 | 4.5 | 48.6 | 24.4 | 8.3 | 5.5 | 484 | 0.76 |
| Non-distilled bottom fraction | 29.5 | 2.3 | 27.2 | 30.8 | 12.9 | 7.6 | 479 | 0.92 |
| Fraction I (35) | 96.6 | 8.9 | 87.7 | 2.2 | — | — | 17 | 0.7 |
| Condensate (50) | 95.6 | 11.8 | 83.8 | 0.8 | — | — | 487 | 0.36 |

TABLE 2-continued

Composition of Product Streams

| | Diphenylmethane-Diisocyanate Isomers | | | Polyphenylene-Polymethylene-Polyisocyanate Oligomers With | | | Hydrolyzable | |
|---|---|---|---|---|---|---|---|---|
| | Total % | 2,4'- % | 4,4'- % | 3-nuclei % | 4-nuclei % | 5-nuclei % | Chlorine ppm | Uretdiones % |
| Example 2: | | | | | | | | |
| Feed | 44.9 | 3.5 | 41.4 | 24.6 | 9.1 | 6.0 | 454 | 3.9 |
| Non-distilled bottom fraction | 23.6 | 1.4 | 22.2 | 32.0 | 12.4 | 8.3 | 561 | 1.1 |
| Fraction I (35) | 96.4 | 6.6 | 89.8 | 2.4 | — | — | 7.1 | 0.36 |
| Condensate (50) | 97.2 | 12.4 | 84.7 | 1.8 | — | — | 870 | 1.68 |
| Comparison Example: | | | | | | | | |
| Feed | 49.4 | 3.6 | 45.8 | 22.9 | 7.4 | 2.7 | 487 | 0.8 |
| Non-distilled bottom fraction | 30.3 | 2.1 | 28.2 | 30.9 | 11.7 | 6.6 | 325 | 0.84 |
| Total distillate | 98.1 | 7.2 | 90.9 | 1.6 | — | — | 187 | 0.24 |

EXAMPLES 3 AND 4

Example 3: Fraction I of Example 1 is separated in a distillation column with the overhead fraction being condensed in a single stage and the side fraction being condensed in two stages. Ninety-one weight percent of the vapors relative to the weight of the side fraction are condensed in the first condensation stage.

Example 4: Fraction I of Example 2 is separated in a distillation column with the overhead fraction being condensed in a single stage and the side fraction being condensed in one stage in the presence of nitrogen.

The reaction conditions are summarized in Table 3 and the compositions of the product streams are compiled in Table 4.

TABLE 3

Examples 3 and 4, Reaction Conditions

| Example | | 3 | 4 |
|---|---|---|---|
| Fraction I according to the Example | | 1 | 2 |
| Feed quanity | [Kg/h] | 16 | 17.7 |
| Overhead fraction (single-stage condensation) Condensate (85) | [kg/h] | 2.5 | 2.4 |
| Condensation temperature in Condenser (75) | [°C.] | 45 | 45 |
| Reflux Quanity | [kg/h] | 36 | 32.5 |
| Total sode fraction, First Condensation stage | [kg/h] | 10.5 | 11.4 |
| Condensation temperature (100) | [°C.] | 150 | — |
| Condensate quanity (110) | [kg/h] | 10.0 | — |
| Second condensation stage | | | |
| Condensation temperature (115) | [°C.] | 45 | 45 |
| Condensate quantity (125) | [kg/h] | 0.5 | — |
| Sump fraction - circulation (70) | [kg/h] | 2000 | 2000 |
| Temperature at column head | [°C.] | 196 | 198 |
| Sump temperature | [°C.] | 211 | 209 |
| Pressure | [mbar] | 4 | 4.25 |
| Nitrogen added to first condensation stage (100) | [NL/h] | — | 65 |

TABLE 4

Composition of Product Streams

| | Diphenylmethane-Diisocyanate Isomers | | | Polyphenylene Polymethylene-Polyisocyanate Oligomers With | | | Hydrolyzable | |
|---|---|---|---|---|---|---|---|---|
| | Total % | 2,4'- % | 4,4'- % | 3-nuclei % | 4-nuclei % | 5-nuclei % | Chlorine ppm | Uretdiones % |
| Example 3: | | | | | | | | |
| Feed | 96.4 | 6.6 | 89.8 | 2.4 | — | — | 7.1 | 0.36 |
| Condensate (85) | 99.6 | 43.8 | 55.4 | — | — | — | 5.8 | 0.24 |
| Condensate (110) | 99.4 | 0.49 | 99.0 | — | — | — | 5 | 0.2 |
| Condensate (125) | 99.3 | 0.4 | 98.9 | — | — | — | 250 | 0.22 |
| Sump fraction (70) | 84.6 | 0.1 | 84.5 | 12.6 | 1.0 | 1.8 | 113 | 1.32 |
| Example 4: | | | | | | | | |
| Feed | 95.1 | 7.2 | 87.9 | 2.3 | — | — | 14 | 0.24 |
| Condensate (85) | 99.1 | 38.7 | 60.4 | — | — | — | 18 | 0.27 |
| Condensate (110) | 99.3 | 0.1 | 99.2 | — | — | — | 34 | 0.28 |
| Sump fraction (70) | 68 | 0.1 | 68.0 | 28.2 | 1.3 | — | 143 | 1.79 |

The embodiments of this invention in which an exclusive privilege or property is claimed are defined as follows:

1. A process for the manufacture of a mixture of diphenylmethane diisocyanate isomers and particularly 4,4'-diphenylmethane diisocyanate containing a small amount of uretdiones and hydrolyzable chlorine by the distillation of a mixture of crude MDI, diphenylmethane diisocyanate isomers and polyphenylene polymethylene polyisocyanates, which comprises:

A. feeding crude MDI into an evaporator at temperatures of 175° C. to 210° C. under reduced pressure, B. discharging a non-distilled bottom fraction of from 97 weight percent to 50 weight percent based on the feed amount of crude MDI, C. evaporating a head fraction of from 3 weight percent to 50 weight percent based on the feed amount of crude MDI, D. condensing from the head fraction a fraction I of from 90 weight percent to 99 weight percent based on the feed amount of the head fraction, in a condensation stage I, at a temperature of from 130° C. to 170° C., the fraction I containing at least 96 weight percent, based on the weight of fraction I, of diphenylmethane diisocyanate isomers, less than one weight percent, based on the weight of fraction I, of uretdiones and less than 50 ppm based on the weight of fraction I of hydrolyzable chlorine, and E. condensing the remaining 10 weight percent to one weight percent, based on the feed amount of head fraction, in a condensation stage II at a temperature of from 45° C. to 60° C.

2. The process of claim 1 which further comprises countercurrently feeding an inert gas through the condensation stage I.

3. The process of claim 1, wherein fraction I is separated in a subsequent distillation column, which further comprises condensing the side fraction, optionally in two stages, and in the presence of an inert gas, condensing the overhead fraction, optionally in two stages and in the presence of an inert gas, and discharging a sump fraction.

4. The process of claim 3 in which the side fraction is condensed in the first stage at a temperature of from 130° C. to 170° C. and in the second stage at a temperature of from 45° C. to 60° C.

5. The process of claim 3 in which the remaining head fraction of condensation stage II and the second condensation stage feed of the overhead fraction and side fraction of the distillation column are combined and that the condensation is carried out in a condensor.

6. The process of claim 1 which further comprises feeding an inert gas through the evaporator.

* * * * *